United States Patent
Ohrbom et al.

(10) Patent No.: US 6,624,275 B2
(45) Date of Patent: *Sep. 23, 2003

(54) WATER- AND ORGANIC-SOLUBLE CARBAMATE MATERIAL

(75) Inventors: Walter H. Ohrbom, Hartland Township, MI (US); Patricia A. Herrel, Hartland Township, MI (US); David J. Law, Livonia, MI (US)

(73) Assignee: BASF Corporation, Southfield, MI (US)

( * ) Notice: Subject to any disclaimer, the term of this patent is extended or adjusted under 35 U.S.C. 154(b) by 43 days.

This patent is subject to a terminal disclaimer.

(21) Appl. No.: 10/002,807

(22) Filed: Nov. 2, 2001

(65) Prior Publication Data

US 2003/0091832 A1 May 15, 2003

(51) Int. Cl.⁷ .............................................. C08F 118/02
(52) U.S. Cl. .................. 526/320; 526/319; 526/321; 526/325; 428/423.1; 428/480; 428/500; 428/704
(58) Field of Search ............... 428/423.1, 480, 428/500, 704; 526/319, 320, 321, 325

(56) References Cited

U.S. PATENT DOCUMENTS

| | | | |
|---|---|---|---|
| 5,336,566 A | 8/1994 | Rehfuss | 428/524 |
| 5,356,669 A | 10/1994 | Rehfuss et al. | 427/407.1 |
| 5,451,656 A | 9/1995 | Menovcik et al. | 528/288 |
| 5,508,379 A | 4/1996 | Menovcik et al. | 528/367 |
| 5,512,639 A | 4/1996 | Rehfuss | 428/524 |
| 5,532,061 A | 7/1996 | Menovcik et al. | 428/423.1 |
| 5,639,828 A | 6/1997 | Briggs et al. | 525/208 |
| 5,693,723 A | 12/1997 | Green | 525/481 |
| 5,693,724 A | 12/1997 | Green | 525/481 |
| 6,414,146 B1 | 7/2002 | Takaeyama et al. | 544/221 |
| 2002/0010254 A1 | 1/2002 | Ramesh et al. | |
| 2002/0103319 A1 * | 8/2002 | Ohrbom et al. | 526/312 |

FOREIGN PATENT DOCUMENTS

EP 915 113 10/1998 ........... C08G/18/38

OTHER PUBLICATIONS

International Search Report PCT/US 02/24810 filed May 8, 2002.

* cited by examiner

Primary Examiner—Nathan M. Nutter
Assistant Examiner—Travis B Ribar
(74) Attorney, Agent, or Firm—Anna M. Budda

(57) ABSTRACT

A carbamate-functional compound having a structure

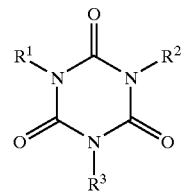

in which each of $R^1$, $R^2$, and $R^3$ is carbamate-functional is water soluble. Coating compositions, especially waterborne coating compositions, include the carbamate-functional compound and one or more crosslinkers. The invention further provide a coating prepared from the coating composition and a coated substrate, especially an automotive substrate, having the coating thereon.

18 Claims, No Drawings

WATER- AND ORGANIC-SOLUBLE CARBAMATE MATERIAL

FIELD OF THE INVENTION

This invention concerns carbamate-functional materials and curable coating compositions containing such materials, especially waterborne coating compositions containing such materials.

BACKGROUND OF THE INVENTION

Carbamate-functional materials have found particular utility in coating compositions as crosslinkable resins. Curable coating compositions utilizing carbamate-functional resins are described, for example, in U.S. Pat. Nos. 5,693,724, 5,693,723, 5,639,828, 5,512,639, 5,508,379, 5,451,656, 5,356,669, 5,336,566, and 5,532,061, each of which is incorporated herein by reference. These coating compositions can provide significant advantages over other coating compositions, such as hydroxy-functional acrylic/melamine coating compositions. For example, the coatings produced using carbamate-functional resins typically have excellent resistance to environmental etch (also called acid etch). Environmental etch results in spots or marks on or in the coating that often cannot be rubbed out.

One drawback of coatings with carbamate-functional resins is that they tend to require more organic solvent to achieve acceptable viscosity and for application. Carbamate-functional materials prepared from an isocyanurate of a diisocyanate, for example, are generally advantageous as an additive resin or principal resin in a coating composition, but these materials increase the viscosity of the coating composition so that more solvent is required. Coatings with higher amounts of organic solvent produce more regulated emissions during application.

Aqueous coating compositions have gained prominence due to the regulations on organic emissions. Such coatings have tended to be water-sensitive, however, because of the presence of the hydrophilic groups used to disperse the binder resins or surfactants, such as polyether-based surfactants, that remain in the coating film as low molecular weight, hydrophilic materials.

It would be advantageous to provide a water-dispersible, carbamate-functional material for a coating composition that would not have water-sensitivity in a cured coating.

SUMMARY OF THE INVENTION

The invention provides a carbamate-functional compound that is water soluble and coating compositions, especially waterborne coating compositions, containing the carbamate-functional material. The invention further provide a coating prepared from the coating composition and a coated substrate, especially an automotive substrate, having the coating thereon.

The carbamate functional compound of the invention has a structure

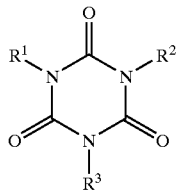

in which each of $R^1$, $R^2$, and $R^3$ is independently

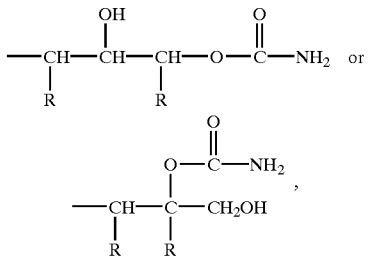

wherein R is hydrogen, methyl, or ethyl.

The carbamate-functional compound of the invention is combined with a carbamate-reactive material to form the coating composition of the invention. The coating composition is applied to a substrate, especially to an automotive substrate, and cured to produce a coating. The coating is preferably the outermost coating on the substrate, particularly a clearcoat coating.

DETAILED DESCRIPTION OF THE INVENTION

The β-hydroxy carbamate compound of the invention may be prepared by reacting triglycidyl isocyanurate first with carbon dioxide to convert the oxirane groups to cyclic carbonate groups, and then with ammonia to convert the cyclic carbonate group to a β-hydroxy carbamate group. Triglycidyl isocyanurate is commercially available or may be prepared by reaction of isocyanuric acid with an epihalohydrin, in particular epichlorohydrin. The reaction of the triglycidyl isocyanurate can be done at any pressure from atmospheric up to supercritical $CO_2$ pressures, but is preferably under elevated pressure (e.g., 60–150 psi). The temperature for this reaction is preferably 60–150° C. Useful catalysts include any that activate an oxirane ring, such as tertiary amine or quaternary salts (e.g., tetramethyl ammonium bromide), combinations of complex organotin halides and alkyl phosphonium halides (e.g., $(CH_3)_3SnI$, $Bu_4SnI$, $Bu_4PI$, and $(CH_3)_4PI$), potassium salts (e.g., $K_2CO_3$, $KI$) preferably in combination with crown ethers, tin octoate, calcium octoate, and the like.

Cyclic carbonate groups can be converted to carbamate groups by reaction with ammonia, which ring-opens the cyclic carbonate to form a β-hydroxy carbamate. The ammonia may be anhydrous ammonia or aqueous ammonia (i.e., $NH_4OH$). The carbonate ring can open to produce either of the two isomeric structures shown above for the $R^1$, $R^2$, and $R^3$ groups.

The β-hydroxy carbamate compound is water soluble and is also soluble in polar organic solvents, such as tetrahydrofuran, alcohols such as methanol and ethanol, and glycol ether-based compounds such as ethylene glycol monobutyl ether, propylene glycol monomethyl ether, and propylene glycol monomethyl ether acetate.

The coating composition of the invention includes the β-hydroxy carbamate compound and one or more crosslinkers or curing agents reactive with the carbamate compound. The coating composition may optionally include other compounds, resins, and/or polymers reactive with the crosslinker. The combination of the β-hydroxy carbamate compound, the crosslinker, and (if present) the optional further compounds, resins, and/or polymers is referred to as the "vehicle."

In preferred embodiments, the β-hydroxy carbamate compound is at least about 5%, more preferably at least about 10%, and still more preferably at least about 15% by weight of the nonvolatile vehicle. It is also preferred for the β-hydroxy carbamate compound to be up to about 30%, more preferably up to about 50%, and still more preferably up to about 70% by weight of the nonvolatile vehicle. The β-hydroxy carbamate compound is preferably from about 10% to about 70%, more preferably from about 15% to about 60%, and still more preferably from about 20% to about 60% by weight of the nonvolatile vehicle.

Particularly useful crosslinkers include, without limitation, materials having active methylol or methylalkoxy groups, such as aminoplast crosslinking agents or phenol/formaldehyde adducts. Examples of preferred curing agent compounds include, without limitation, melamine formaldehyde crosslinkers, including monomeric or polymeric melamine resin and partially or fully alkylated melamine resin, urea resins, and methylol ureas such as urea formaldehyde resin, alkoxy ureas such as butylated urea formaldehyde resin. Another suitable crosslinking agent is tris(alkoxy carbonylamino) triazine (available from Cytec Industries under the trademark TACT). Other useful crosslinkers include, without limitation, polyisocyanates and blocked polyisocyanates, curing agents that have epoxide groups, amine groups, acid groups, siloxane groups, cyclic carbonate groups, and anhydride groups. The curing agent may be combinations of these, particularly combinations that include aminoplast crosslinking agents. At least one crosslinker with functionality reactive with active hydrogens of the β-hydroxy carbamate compound is included. Aminoplast resins such as melamine formaldehyde resins or urea formaldehyde resins are especially preferred. Water-soluble aminoplast resins for aqueous coating compositions are known. These include high imino-content melamine formaldehyde resins and fully methoxylated melamine formaldehyde resins.

In preferred embodiments, the crosslinker is at least about 5%, more preferably at least about 10% by weight of the nonvolatile vehicle. It is also preferred for the crosslinker to be up to about 40%, more preferably up to about 30% by weight of the nonvolatile vehicle. The crosslinker is preferably from about 5% to about 40%, more preferably from about 10% to about 35%, and still more preferably from about 15% to about 35% by weight of the nonvolatile vehicle.

The coating composition may include further crosslinkable compounds, resin, and/or polymers, preferably those that have active hydrogen functionality. Examples of additional compounds, resins, and/or polymers that may optionally be included are other carbamate- or hydroxyl-functional materials, including acrylic polymers, polyurethanes, and polyesters.

The coating composition used in the practice of the invention may include a catalyst to enhance the cure reaction. For example, when aminoplast compounds, especially monomeric melamines, are used as a curing agent, a strong acid catalyst may be utilized to enhance the cure reaction. Such catalysts are well-known in the art and include, without limitation, p-toluene sulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

Although aqueous coating compositions that are free of regulated volatile organic compounds are preferred, a solvent may optionally be utilized in the coating composition used in the practice of the present invention. In general, the solvent can be any organic solvent and/or water. In one preferred embodiment, the solvent is a polar organic solvent. More preferably, the solvent is selected from polar aliphatic solvents or polar aromatic solvents. Still more preferably, the solvent is a ketone, ester, acetate, aprotic amide, aprotic sulfoxide, aprotic amine, or a combination of any of these. Examples of useful solvents include, without limitation, methyl ethyl ketone, methyl isobutyl ketone, m-amyl acetate, ethylene glycol butyl ether-acetate, propylene glycol monomethyl ether acetate, xylene, N-methylpyrrolidone, blends of aromatic hydrocarbons, and mixtures of these. In another preferred embodiment, the solvent is water or a mixture of water with small amounts of co-solvents.

The coating composition according to the invention is preferably utilized in an automotive or industrial high-gloss coating and/or as the clearcoat of an automotive composite color-plus-clear coating. High-gloss coatings as used herein are coatings having a 20° gloss (ASTM D523) or a DOI (ASTM E430) of at least 80.

The coating composition may also be formulated as a pigmented coating, such as for a basecoat coating or a primer coating. In this case, the coating composition further includes a pigment or filler material. The pigment may be any organic or inorganic compounds or colored materials, metallic or other inorganic flake materials such as pearlescent mica flake pigments or metallic flake pigments such as aluminum flake, and other materials of kind that the art normally includes in such coatings. Examples of typical fillers are talc and barytes. Pigments and other insoluble particulate compounds such as fillers are usually used in the composition in an amount of 1% to 100%, based on the total solid weight of binder components (i.e., a pigment-to-binder ratio of 0.1 to 1).

Additional agents, for example surfactants, stabilizers, wetting agents, rheology control agents, dispersing agents, adhesion promoters, UV absorbers, hindered amine light stabilizers, etc. may be incorporated into the coating composition. While such additives are well-known in the prior art, the amount used must be controlled to avoid adversely affecting the coating characteristics.

Coating compositions can be coated on the article by any of a number of techniques well-known in the art. These include, for example, spray coating, dip coating, roll coating, curtain coating, and the like. For automotive body panels, spray coating is preferred.

When the coating composition according to the invention is used as the clearcoat of a composite color-plus-clear coating, the pigmented basecoat composition may any of a number of types well-known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of crosslinkable functional groups. Such groups include, for example, hydroxy, isocyanate, amine, epoxy, acrylate, vinyl, silane, and acetoacetate groups. These groups may be masked or blocked in such a way so that they are unblocked and available for the crosslinking reaction under the desired curing conditions, generally elevated temperatures. Useful crosslinkable functional groups include hydroxy, epoxy, acid, anhydride, silane, and acetoacetate groups. Preferred crosslinkable functional groups include hydroxy functional groups and amino functional groups.

Basecoat polymers may be self-crosslinkable, or may require a separate crosslinking agent that is reactive with the functional groups of the polymer. When the polymer comprises hydroxy functional groups, for example, the crosslinking agent may be an aminoplast resin, isocyanate and blocked isocyanates (including isocyanurates), and acid or anhydride functional crosslinking agents.

The coating compositions described herein are preferably subjected to conditions so as to cure the coating layer. Although various methods of curing may be used, heat-curing is preferred. Generally, heat curing is effected by exposing the coated article to elevated temperatures provided primarily by radiative heat sources. Curing temperatures will vary depending on the particular blocking groups used in the cross-linking agents, however they generally range between 90° C. and 180° C. The first compounds according to the present invention are preferably reactive even at relatively low cure temperatures. Thus, in a preferred embodiment, the cure temperature is preferably between 115° C. and 150° C., and more preferably at temperatures between 115° C. and 140° C. for a blocked acid catalyzed system. For an unblocked acid catalyzed system, the cure temperature is preferably between 80° C. and 100° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following example. The examples are merely illustrative and do not in any way limit the scope of the invention as described and claimed. All parts are parts by weight unless otherwise noted.

EXAMPLE

In a suitable reactor, 2000 grams of a 70% by weight solution of the tricarbonate of triglycidyl isocyanurate (obtained from Vantico; structure

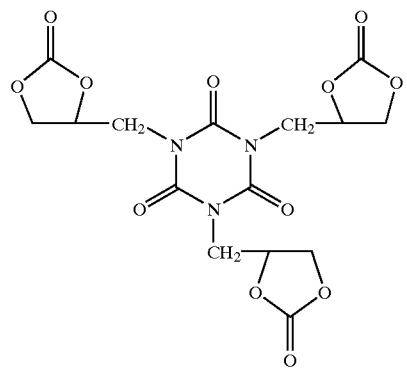

in water was reacted with 1000 grams of concentrated ammonium hydroxide. Ammonia gas was then bubbled into the reaction mixture. When the reaction was complete, excess ammonium hydroxide and a portion of the water were removed by vacuum stripping. Water was then added to obtain a 77.5% nonvolatile by weight solution of the tricarbamate product having having a structure

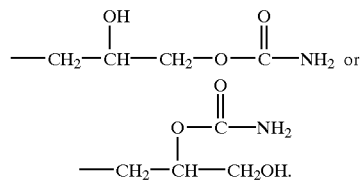

wherein each of $R^1$, $R^2$, and $R^3$ is independently $$-CH_2-\underset{\underset{\text{OH}}{|}}{CH}-CH_2-O-\overset{\overset{O}{\|}}{C}-NH_2 \text{ or}$$

$$-CH_2-\underset{\underset{CH_2OH}{|}}{CH}-\underset{O}{\overset{O-\overset{\overset{O}{\|}}{C}-NH_2}{|}}$$

A clear coating composition was prepared by mixing together 100 grams of the tricarbamate product, 77.8 grams of CYMEL® 327 (a fully methylated melamine, 90% nonvolatile in butanol), 5.6 grams of a solution of dodecylbenzene sulfonic acid (25% active), 18.3 grams of N-methyl pyrrolidinone, and 0.8 grams of a silicone additive. The viscosity of the coating composition was 200 centipoise at 400 $s^{-1}$. The VOC of the coating composition was 1.0 lb./gal.

The clear coating composition was applied over a flashed (dried, but not cured) layer of a basecoat coating composition over an electrocoat primed steel panel in the following way. A 4 mil wet drawdown of the basecoat composition was applied on the electrocoat primed steel panel. The basecoat layer drawdown was flashed for five minutes at 140° F. A 4 to 5 mil wet drawdown layer of the clear coating composition was applied in a layer perpendicular to the basecoat layer drawdown. The panel was flashed for 10 minutes at 110° F., then baked for 20 minutes at 280° F. The baked basecoat layer was 0.8 mils and the baked clearcoat layer was 2.0 to 2.4 mils.

The baked clearcoat layer passed a crosshatch test for adhesion to the basecoat layer. The basecoat/clearcoat composite coating had a hardness of 37 Knoops on a Tukon hardness machine.

The invention has been described in detail with reference to preferred embodiments thereof. It should be understood, however, that variations and modifications can be made within the spirit and scope of the invention.

What is claimed is:

1. A compound having a structure

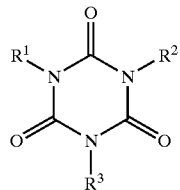

wherein each of $R^1$, $R^2$, and $R^3$ is independently

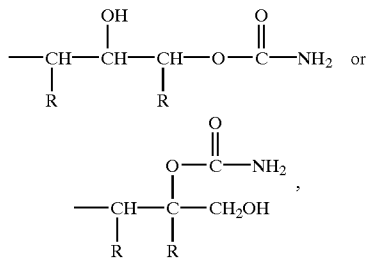

wherein R is hydrogen, methyl, or ethyl.

2. An aqueous composition, comprising water end the compound of claim 1.

3. A coating composition, comprising the compound of claim 1 and at least one crosslinker reactive with carbamate functionality.

4. A coating composition according to claim 3, wherein the crosslinker is a melamine formaldehyde resin.

5. The coating composition according to claim 3, wherein the coating composition is aqueous.

6. The coating composition according to claim 3, wherein the composition includes from about 5% to about 70% by weight of the compound of claim 1.

7. The coating composition according to claim 3, wherein the composition includes from about 20% to about 60% by weight of the compound of claim 1.

8. The coating composition according to claim 3, wherein the composition is a clearcoat coating composition.

9. A coating on a substrate, comprising a layer of the cured composition of claim 3.

10. A composite coating on a substrate, comprising a layer of basecoat coating and a layer of the cured clearcoat coating composition of claim 8.

11. A coating composition according to claim 3, further comprising e member selected from the group consisting of acrylic polymers, polyurethanes, and polyesters.

12. A costing composition according to claim 11, wherein the crosslinker is a melamine formaldehyde resin.

13. The coating composition according to claim 11, wherein the coating composition is aqueous.

14. The coating composition according to claim 11, wherein the composition includes from about 5% to about 70% by weight of the compound of claim 1.

15. The coating composition according to claim 11, wherein the composition includes from about 20% to about 60% by weight of the compound of claim 1.

16. The coating composition according to claim 11, wherein the composition is a clearcoat coating composition.

17. A coating on a substrate, comprising a layer of the cured composition of claim 11.

18. A composite coating on a substrate, comprising a layer of basecoat coating and a layer of the cured clearcoat coating composition of claim 16.

* * * * *